United States Patent
Raju

(10) Patent No.: US 6,558,060 B1
(45) Date of Patent: May 6, 2003

(54) CATHETER GUIDEWIRE LUBRICATING DEVICE

(76) Inventor: Seshadri Raju, 1020 River Oaks Dr., Suite 420, Jackson, MS (US) 39208

( * ) Notice: Subject to any disclaimer, the term of this patent is extended or adjusted under 35 U.S.C. 154(b) by 0 days.

(21) Appl. No.: 10/045,750

(22) Filed: Jan. 11, 2002

(51) Int. Cl.[7] ............................................. A46B 11/00
(52) U.S. Cl. ............................................. 401/10; 401/9
(58) Field of Search .................................. 401/10, 9, 11, 401/12, 196, 205

(56) References Cited

U.S. PATENT DOCUMENTS

| | | | |
|---|---|---|---|
| 2,908,923 A | * 10/1959 | Schlechter | 401/10 |
| 3,048,878 A | * 8/1962 | Gray et al. | 401/10 |
| 3,535,047 A | * 10/1970 | Vireno | 401/10 |
| 4,347,010 A | * 8/1982 | Petkoff | 401/10 |
| 5,460,616 A | * 10/1995 | Weinstein et al. | 604/167 |
| 5,549,576 A | * 8/1996 | Patterson et al. | 604/247 |

* cited by examiner

Primary Examiner—David J. Walczak
(74) Attorney, Agent, or Firm—Jones, Walker, Waechter Poitevent, Carrere & Denegre, LLP

(57) ABSTRACT

In conjunction with a guidewire, a handheld guidewire lubrication device. The device has a fluid reservoir for storing a lubricating fluid, where the reservoir has an exterior surface with a first and second face portions, and the reservoir is flexible to allow the first and second face portions to be brought into opposition. The first and second face portions have a compressible permeable material positioned on the face portions, and the compressible material is in fluid communication with the interior of the reservoir.

9 Claims, 1 Drawing Sheet

CATHETER GUIDEWIRE LUBRICATING DEVICE

FIELD OF THE INVENTION

This invention relates to the field of lubricating guidewires, such as cardiac catheter guide wires. In particular, this invention provides a simple inexpensive and disposable device for lubricating a catheter guidewire.

BACKGROUND OF THE INVENTION

In various medical procedures, a guidewire is used for guiding a medical device, such as a catheter, which is introduced in to a living body directly or through an endoscope or the like. The inserted medical device, typically having a hollow structure, is used to deliver various medical tools, substances or to perform certain medical procedures in a target location within the body, such as the heart, liver and other organs. The inserted device is generally placed into a body cavity, organ systems, or venous system (an incision may be needed to access certain systems, such as an incision through the skin to access an artery) and guided to the target location by a guidewire. The guidewire is generally a thin wire or hollow tube core, with a flexible outer body such as a helical coil. The outer flexible body is torqued to steer the guidewire to the target location. The device, such as a catheter, may be inserted over the guidewire and steered to the target location, either in conjunction with the placement of the guidewire, or after placement of the guidewire, by threading the catheter over the previously positioned guidewire. Examples of guidewires can be found in U.S. Pat. Nos. 6,296,616 and 6,251,085 herein incorporated by reference. When a guidewire is inserted into the vascular system, an introducer is used, which generally incorporates a type of homeostatic valve mechanism to isolate the vascular system and provide an entry point for the guidewire. Some introduces include a lubricating device, such as a sponge within the introducer which lubricates the guidewire/catheter through the valve/opening of the introducer. Newer guidewires can be coated with a hydrophobic coating, thereby providing a very slick surface when water is used to lubricate the coated guidewire.

A catheter will be threaded, sleeved or inserted over the guidewire, through the lumen of the catheter. When threading or inserting the catheter onto the guidewire, lubrication is also needed, as the catheter lumen's diameter will generally be close to that of the guidewire. Currently, the guidewire is wetted by applying a lubricating fluid via a sponge to the guidewire during catheter insertion, requiring the sponge to be continually re-dipped into the wetting lubricating fluid during the procedure. This is cumbersome and presents risks of contamination.

OBJECTS OF THE INVENTION

It is an object of the invention to provide a simple inexpensive device for lubricating a guidewire.

It is another object of the invention to provide a disposable device for lubricating a guidewire.

It is another object of the invention to provide an automatic feed device for lubricating a guidewire.

SUMMARY OF THE INVENTION

In conjunction with a guidewire, a handheld guidewire lubrication device is provided. The device has a fluid reservoir for storing a lubricating fluid, where the reservoir has an exterior surface with a first and second face portions, and the reservoir is flexible to allow the first and second face portions to be brought into opposition. The first and second face portions have a compressible permeable material positioned on the face portions, and the compressible material is in fluid communication with the interior of the reservoir.

DETAILED DESCRIPTION OF THE INVENTION

Figure 1A:
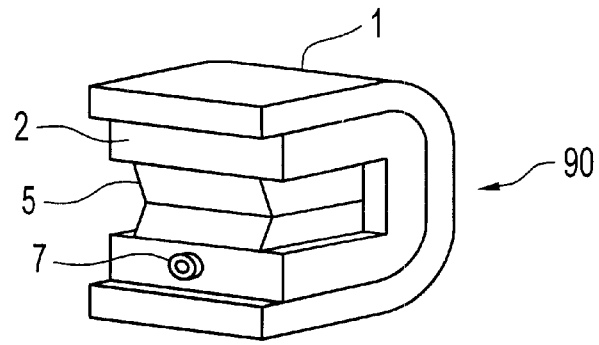
FIG. 1A shows an isometric drawing of one embodiment of the invention.
Figure 1B:
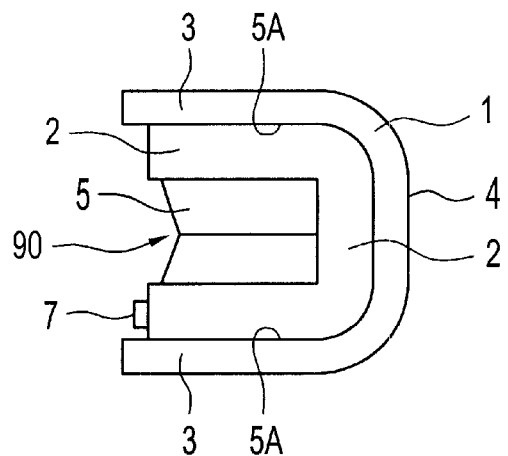
FIG. 1B shows a side view of FIG. 1.
Figure 2:
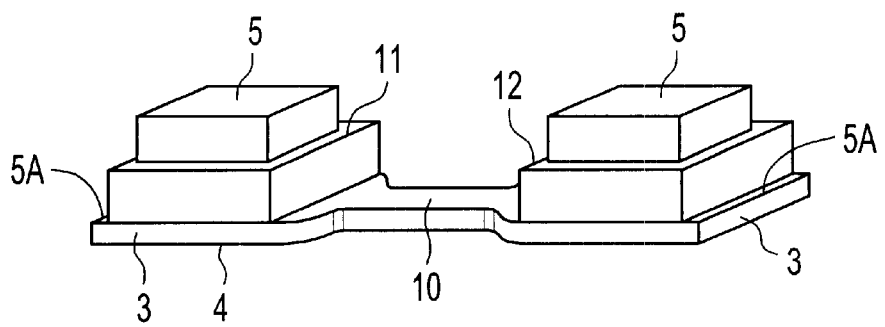
FIG. 2 shows an isometric drawing of another embodiment of the invention.

Shown in FIG. 1 is one embodiment of a guidewire lubricating device. The device has a backing 1, which may be constructed from a semi-rigid plastic and shaped as "U" or "V" shaped, having two legs 3 and a bottom 4. The U shape leaves the reservoir with an opening at the top, the open in the "U." The two legs 3 have interior walls 5A, opposed to each other. Placed on the backing 1, or making up the part or all of the backing, is a reservoir 2 which may be constructed of a semi-rigid plastic. The reservoir is designed to hold lubricating fluid for dispensing. The reservoir may be the entire "U," one of the legs of the "U," or a part of the "U." Additionally, the reservoir 2 may be integrated with the backing 1 or part of the backing 1. It is preferred that the bottom portion 2 of the "U" be flexible, enabling the two legs of the "U" shape to be squeezed together, as later described. Additionally, instead of a "U" shape, the device could be linear (see FIG. 2a), however, in this case, the device still has a flexible section 10, enabling the device to be folded into a U shaped configuration with opposing facing walls 11 and 12. A linear configuration may assist in packaging and storing the device for use.

As shown in FIG. 1, reservoir may be fillable through cap 7 or other device. Alternatively, during manufacturing, the reservoir may be pre-filled with sterile lubricating fluids and sealed, preventing contamination that might be caused by filling on site. As shown in FIG. 1, located on the interior walls of the backing or reservoir is a compressible lubricating dispensing material 5, such as a sponge or open cell foam material. The dispensing material is in fluid contact with a permeable region of the reservoir. The permeable region can consist of a series of openings in the reservoir, or a separate permeable membrane making up a portion of the reservoir surface. The fluid dispensing material may be in two, one on each opposing face, or be "U" or "V" shaped, as shown in FIG. 1. It is preferred that the dispensing material have a slot or slit 90, into the material (or created by using two opposing pieces of material). Alternate configurations are possible (a slot not through the material, but created between the between the material and the backing or reservoir), such is not preferred. It is preferred that the device be small enough to be held between by the thumb and index finger, (pr thumb and index and middle finger) and may have an finger slips attached to or positioned on the exterior surfaces of the opposing faces (such as a loop or quarter sphere) into which a finger tip could be inserted to assist in holding the device, particularly if the wetting fluid is extremely slick.

In use, the device can be a disposable device, as it is inexpensive to make. The device can come from the manufacturer filled with sterile fluid in sterile shrink-wrap or other packaging. To use the device, the device must have lubricating fluid (sterile water, or other type of suitable lubricating fluid). The legs of the U should be squeezed to prime the dispensing material with lubricating fluid. The guidewire would be placed in the slot, and the device run back and forth along the guidewire to lay down a layer of lubricating fluid over the guidewire. The catheter or other target device would be placed over the lubricated guidewire, and inserted into the introducer, if supplied by the procedure, and directed to the target location. After suitable location of the catheter or other device, a portion of the guidewire may be exposed outside the body. If an exchange is later required (i.e. replacing the targeted tool or device with a different target device) the surgeon would lubricating the exposed guidewire portion, withdraw the device over the guidewire (leaving the guidewire in place) and re-move the device from the guidewire, re-lubricate the guidewire, and install the new device or catheter over the guidewire and then position the newly installed device (through transit over the guidewire) to the desired target location.

As should be appreciated from the foregoing, the lubricating device is simple, inexpensive to manufacture, disposable due to its low manufacturing costs, and in use, does not have to be re-wetted due to the reservoir, and thus, helps to prevent contamination.

I claim:

1. The combination of a guidewire and a handheld guidewire lubrication device, the handheld guidewire lubrication device comprising a fluid reservoir having an interior for storing a lubricating fluid, said reservoir having an exterior surface having first and second face portions being opposed, a compressible permeable material disposed on said first and said second face portions and in fluid communication with said interior of said reservoir, said reservoir being adapted to allow a user to compress said reservoir whereby said opposing first and second face portions are moved into closer proximity.

2. A handheld guidewire lubrication device according to claim 1 where said reservoir has two legs portions defining a "U" or "V" shape having an open top, said "U" or "V" shape defining an interior facing surface of said two legs.

3. A handheld reservoir guidewire lubrication device according to claim 2 wherein said reservoir has a semi-rigid backing positioned on the exterior surface of said legs.

4. A handheld reservoir guidewire lubrication device according to claim 2 where said reservoir further has a semi-rigid backing positioned on the non-opposing faces of said legs.

5. A handheld reservoir guidewire lubrication device according to claim 2 wherein said compressible material is positioned on said interior leg portions, said lubrication device having a slot defined from said open top of said reservoir, through said material parallel to said legs, thereby allowing for insertion of said guidewire into said slot through said open top of said reservoir.

6. A handheld reservoir guidewire lubrication device according to claim 1 wherein said reservoir is constructed of semi-rigid plastic.

7. A handheld reservoir guidewire lubrication device according to claim 1 wherein said permeable compressible material is a sponge-like material.

8. A handheld reservoir guidewire lubrication device according to claim 1 where said reservoir first and second face portions are connected by a semi-flexible band.

9. A handheld reservoir guidewire lubrication device according to claim 1 where said device is adapted to be securely held between the thumb and index finger of a user.

* * * * *